United States Patent [19]
Pool et al.

[11] Patent Number: 5,741,803
[45] Date of Patent: Apr. 21, 1998

[54] SUBSTITUTED THIAZOLIDINEDIONLE DERIVATIVES

[75] Inventors: Colin Ripley Pool, Surrey; Alan William Tremper, Kent; Malcolm David Brightwell; Robin Sherwood Roman, both of Surrey, all of England

[73] Assignee: SmithKline Beecham plc, Brentford, England

[21] Appl. No.: 465,509

[22] Filed: Jun. 5, 1995

Related U.S. Application Data

[63] Continuation of Ser. No. 392,878, Mar. 3, 1995, abandoned, filed as PCT/GB93/01853, Sep. 1, 1993.

[30] Foreign Application Priority Data

Sep. 5, 1992 [GB] United Kingdom .................. 9218830

[51] Int. Cl.⁶ .................................................. A61K 31/44
[52] U.S. Cl. ........................................ 514/342; 546/269.7
[58] Field of Search .......................... 514/342; 546/269.7

[56] References Cited

U.S. PATENT DOCUMENTS

| | | | |
|---|---|---|---|
| 4,197,297 | 4/1980 | Weinstock | 514/218 |
| 5,002,953 | 3/1991 | Hindley | 514/275 |
| 5,039,687 | 8/1991 | Effland et al. | 514/343 |

FOREIGN PATENT DOCUMENTS

| | | |
|---|---|---|
| 193 256 | 9/1986 | European Pat. Off. |
| 0 306 228 A1 | 3/1989 | European Pat. Off. |
| 0 419 035 A1 | 3/1991 | European Pat. Off. |

OTHER PUBLICATIONS

Berge et al. Journal of Pharmaceutical Sciences, vol. 66, No. 1, Jan. 1977. Review Article: Pharceutical Salts.

*Primary Examiner*—Jane Fan
*Attorney, Agent, or Firm*—Charles M. Kinzig; Edward T. Lentz

[57] ABSTRACT

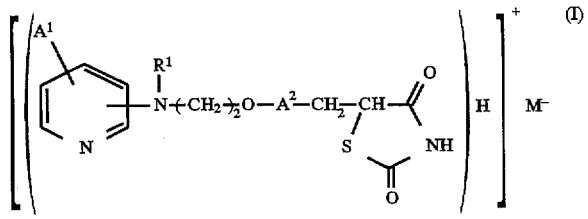

A compound of formula (I) or a tautomeric form therof and/or a pharmaceutically acceptable solvate thereof, wherein R1,A1,A2,M are as defined in the, specification. A process for preparing such a compound, a pharmaceutical composition containin such a compound and the use of such a compound for treating hyperglycemia.

5 Claims, No Drawings

SUBSTITUTED THIAZOLIDINEDIONLE DERIVATIVES

This is a continuation of application Ser. No. 08/392,878, filed Mar. 3, 1995 now abandoned, which is a 371 of PCT/GB 93/01853 Sep. 1, 1993 now Ser. No. 94/05659.

This invention relates to certain novel compounds, to a process for preparing such compounds, to pharmaceutical compositions containing such compounds and to the use of such compounds and compositions in medicine.

European Patent Application, Publication Number 0,306, 228 relates to certain thiazolidinedione derivatives disclosed as having hypoglycaemic and hypolipidaemic activity.

It is now surprisingly indicated that a specific group of compounds from within formula (I) of EP-A-0,306,228 have improved selectivity of action and are therefore of particular use in the treatment of Type II diabetes. These compounds are also indicated to be of particular use for the treatment and/or prophylaxis of other diseases including hyperlipidaemia, hypertension and cardiovascular disease, especially atherosclerosis. In addition these compounds are considered to be useful for treating certain eating disorders, in particular the regulation of appetite and food intake in subjects suffering from disorders associated with under-eating, such as anorexia nervosa, and disorders associated with over-eating, such as obesity and anorexia bulimia.

These compounds show good aqueous stability and good stability in the solid form, certain of these compounds are indicated to be particularly stable. In addition these compounds are significantly more soluble in water than the corresponding free base.

The surprising and advantageous stability and aqeous solubility of these compounds provides for significant formulation and bulk handling advantages.

Accordingly, the present invention provides a compound of formula (I):

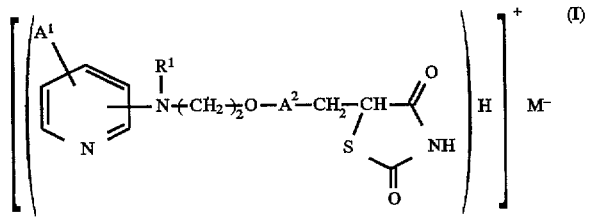

or a tautomeric form thereof and/or a pharmaceutically acceptable solvate thereof, wherein:

$R^1$ represents a hydrogen atom, an alkyl group, an acyl group, an aralkyl group, wherein the aryl moiety may be substituted or unsubstituted, or a substituted or unsubstituted aryl group; $A^1$ represents hydrogen or 1 to 4 optional substituents selected from the group consisting of: alkyl, alkoxy, aryl and halogen or $A^1$ represents two substituents on adjacent carbon atoms, which substituents together with the carbon atoms to which they are attached form a substituted or unsubstituted aryl group; $A^2$ represents a benzene ring having 1 to 3 optional substituents; and $M^-$ represents a counter-ion.

Suitable counter-ions $M^-$ include ions provided by pharmaceutically acceptable acids.

A suitable source of counter-ions $M^-$ is provided by those pharmaceutically acceptable acids having a $pK_a$ in the range of from 0.1 to 4.5 and especially in the range of from 1.75 to 2.5.

Favoured pharmaceutically acceptable acids include mineral acids, such as hydrobromic, hydrochloric and sulphuric acids, and organic acids, such as methanesulphonic, tartaric and maleic acids, especially tartaric and maleic acid.

A preferred counter-ion is the maleate ion $HOOC.CH=CH.COO^-$.

Preferably, $A^1$ is hydrogen.

Suitable optional substituents for the moiety $A^2$ include up to three substituents selected from halogen, substituted or unsubstituted alkyl or alkoxy.

Favourably, $A^2$ represents a moiety of formula (e):

wherein $R^2$ and $R^3$ each independently represent hydrogen, halogen, substituted or unsubstituted alkyl or alkoxy.

Suitably, $R^2$ and $R^3$ each independently represent hydrogen, halogen, alkyl or alkoxy.

Preferably, $R^2$ and $R^3$ each represent hydrogen.

Suitably, $R^1$ represents hydrogen, alkyl, acyl, especially acetyl, or benzyl.

Preferably, $R^1$ represents an alkyl group, for example a methyl group.

Preferably the moiety:

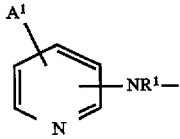

in formula (I) is a moiety of formula:

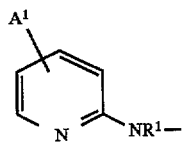

wherein $A^1$ and $R^1$ are as defined above

A preferred compound of formula (I) is 5-[4-[2-(N-methyl-N-(2-pyridyl)amino)ethoxy]benzyl]thiazolidine-2, 4-dione maleic acid salt.

The compounds of formula (I) are salts. The present invention extends to all forms of such salts including those provided by association of the salting hydrogen with all possible salt forming parts of the molecule and especially that provided by association with the pyridine nitrogen.

As indicated above a compound of formula (I) may exist in one of several tautomeric forms, all of which are encompassed by the present invention. It will be appreciated that the present invention encompasses all of the isomeric forms of the compounds of formula (I) and the pharmaceutically acceptable salts thereof, including any stereoisomeric forms thereof, whether as individual isomers or as mixtures of isomers.

When used herein the term 'aryl' includes phenyl and naphthyl optionally substituted with up to five, preferably up to three, groups selected from halogen, alkyl, phenyl, alkoxy, haloalkyl, hydroxy, nitro, alkoxycarbonyl, alkoxycarbonylalkyl, alkylcarbonyloxy, or alkylcarbonyl groups.

When used herein the term 'halogen' refers to fluorine, chlorine, bromine and iodine; preferably chlorine.

Suitable alkyl groups, including alkyl groups per se and alkyl groups that form part of other groups such as alkoxy groups, are $C_{1-12}$ alkyl groups having straight or branched carbon chains, especially $C_{1-6}$ alkyl groups e.g. methyl, ethyl, n-propyl, iso-propyl, n-butyl, isobutyl or tert-butyl groups.

Suitable substituents for any alkyl group include those indicated above in relation to the term "aryl".

Suitable acyl groups include alkylcarbonyl groups.

Suitable pharmaceutically acceptable solvates include hydrates.

In a further aspect the present invention also provides a process for the preparation of a compound of formula (I), or a tautomeric form thereof, and/or a pharmaceutically acceptable solvate thereof, which process comprises reacting a compound of formula (II):

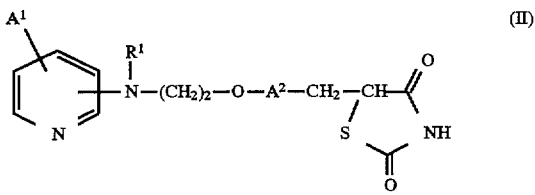

wherein $R^1$, $A^1$ and $A^2$ are as defined in relation to formula (I), with a source of above defined counter-ion $M^-$; and thereafter if required preparing a pharmaceutically acceptable solvate thereof.

A suitable source of a counter-ion $M^-$ is a pharmaceutically acceptable acid.

A suitable source of counter-ions includes pharmaceutically acceptable acids having a $pK_a$ in the range of from 1.5 to 4.5, especially in the range of from 1.75 to 2.5.

Favoured pharmaceutically acceptable acids include mineral acids, such as hydrobromic, hydrochloric and sulphuric acids, and organic acids, such as methanesulphonic, tartaric and maleic acids.

A preferred source of a counter-ion is maleic acid.

The reaction between the compound of formula (I) and the source of counter-ion $M^-$ is generally carried out under conventional salt forming conditions, for example by admixing the compound of formula (I) and the source of counter-ion $M^-$, suitably in approximately equimolar amounts but preferably using a slight excess of the source of counter-ion $M^-$, in a solvent, generally a $C_{1-4}$ alkanolic solvent such as ethanol, at any temperature which provides a suitable rate of formation of the required product, generally at an elevated temperature for example at the reflux temperature of the solvent and thereafter crystallising the required product.

Pharmaceutically acceptable solvates of the compound of formula (I) may be prepared using conventional chemical procedures.

The compound of formula (II) may be prepared according to methods disclosed in EP-A-0306228.

Suitable sources of counter-ion are known commercially available sources, such as maleic acid, or the required source may be prepared according to known procedures.

Where appropriate the isomeric forms of the compounds of formula (I) and the pharmaceutically acceptable salts thereof may be prepared as individual isomers using conventional chemical procedures.

The stability of the compounds of the invention may be determined using conventional quantitative analytical methods: For example the stability of the compounds in the solid form may be determined by using accelerated stability tests such as differential scanning calorimetry (DSC), thermogravimetric analysis (TGA) and isothermal testing at elevated temperatures including conventional storage tests wherein the test compounds are stored under controlled conditions of temperature and humidity over known periods of time. Quantitative analysis of the test compounds, against appropriate reference standards before, during and after the storage period allows the stability of the test compound to be determined.

As stated the compounds of the invention are significantly more soluble in water than the corresponding free base. Thus a convenient method for determining the stability of the compounds of the invention in aqueous solution involves determining the degree of precipitation of the parent free base from an aqueous solution of the test compound at known conditions of temperature and over known periods of time. We have found that the compounds of formula (I) show good aqueous stability. In particular the compounds of formula (I) wherein $M^-$ represents maleate or tartrate are particularly stable in aqueous solution. Most surprisingly, the compounds of formula (I) wherein $M^-$ represents a maleate ion, $HOOC.CH=CH.COO^-$, were found to be particularly stable in aqueous solution.

The quantitative analysis of the test compounds in the above mentioned tests may be carried out using conventional methods, generally chromatographic methods such as high pressure liquid chromatography.

As mentioned above the compounds of the invention are indicated as having useful therapeutic properties:

The present invention accordingly provides a compound of formula (I), and/or a pharmaceutically acceptable solvate thereof, for use as an active therapeutic substance.

Thus the present invention provides a compound of formula (I), or a tautomeric form thereof and/or a pharmaceutically acceptable solvate thereof, for use in the treatment of and/or prophylaxis of hyperglycaemia.

In a further aspect the present invention also provides a compound of formula (I), or a tautomeric form thereof and/or a pharmaceutically acceptable solvate thereof, for use in the treatment and/or prophylaxis of hyperlipidaemia.

As indicated hereinbefore the present invention also provides a compound of formula (I) or a tautomeric form thereof and/or a pharmaceutically acceptable solvate thereof for use in the treatment of hypertension, cardiovascular disease and certain eating disorders.

Cardiovascular disease includes in particular atherosclerosis.

Certain eating disorders include in particular the regulation of appetite and food intake in subjects suffering from disorders associated with under-eating, such as anorexia nervosa, and disorders associated with over-eating, such as obesity and anorexia bulimia.

A compound of formula (I), or a tautomeric form thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of formula (I), or a tautomeric form thereof, or a pharmaceutically acceptable solvate thereof, and a pharmaceutically acceptable carrier therefor.

As used herein the term 'pharmaceutically acceptable' embraces compounds, compositions and ingredients for both human and veterinary use: for example the term 'pharmaceutically acceptable salt' embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate or sodium lauryl sulphate.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

The present invention further provides a method for the treatment and/or prophylaxis of hyperglycaemia in a human or non-human mammal which comprises administering an effective, non-toxic, amount of a compound of formula (I), or a tautomeric form thereof and/or a pharmaceutically acceptable solvate thereof to a hyperglycaemic human or non-human mammal in need thereof.

The present invention further provides a method for the treatment of hyperlipidaemia in a human or non-human mammal, which comprises administering an effective, non-toxic, amount of a compound of formula (I), or a tautomeric form thereof and/or a pharmaceutically acceptable solvate thereof, to a hyperlipidaemic human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemic humans, and/or the treatment and/or prophylaxis of hyperlipidaemic human, the compound of formula (I), or a tautomeric form thereof and/or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg.

In the treatment and/or prophylaxis of hyperglycaemic non-human mammals, especially dogs, the active ingredient may be adminstered by mouth, usually once or twice a day and in an amount in the range of from about 0.025 mg/kg to 25 mg/kg, for example 0.1 mg/kg to 20 mg/kg. Similar dosage regimens are suitable for the treatment and/or prophylaxis of hyperlipidaemia in non-human mammals.

The dosages regimens for the treatment of hypertension, cardiovascular disease and eating disorders will generally be those mentioned above in relation to hyperglycaemia.

In a further aspect the present invention provides the use of a compound of formula (I), or a tautomeric form thereof and/or a pharmaceutically acceptable solvate thereof, for the manufacture of a medicament for the treatment and/or prophylaxis of hyperglycaemia.

The present invention also provides the use of a compound of formula (I), or a tautomeric form thereof and/or a pharmaceutically acceptable solvate thereof, for the manufacture of a medicament for the treatment and/or prophylaxis of hyperlipidaemia, hypertension, cardiovascular disease or certain eating disorders.

The following Example illustrates the invention but does not limit it in any way.

EXAMPLE 1

5-[4-[2-(N-Methyl-N-(2-pyridyl)amino)ethoxy] benzyl]thiazolidine-2,4-dione, maleic acid salt 5-[4-[2-(N-Methyl-N-(2-pyridyl)amino)ethoxy]benzyl] thiazolidine-2,4-dione (470 g) and maleic acid (137 g) were dissolved in ethanol (41.) at boiling. The hot solution was filtered via diatomaceous earth and was then allowed to cool slowly with gentle agitation. After leaving in a refrigerator at 0°–5° C. for several hours, the maleate salt was filtered off, washed with ethanol and dried in vacuo at 50° to give 446 g (73%) of product, m.p. 120°–121° C.

1H NMR δ ($d_6$-DMSO): 3.0–3.35 (2H, complex); 3.10 (3H, s); 3.95 (2H, t); 4.15 (2H, t); 4.85 (1H, complex); 6.20 (2H, s); 6.65 (1H, t); 6.85 (3H, complex); 7.15 (2H, d) 7.65 (1H, t); 8.05 (1H, complex); 11.85–12.1 (1H, broad, exchanges with $D_2O$).

A very broad signal was observed in the range 2–5 ppm which is thought to be due to residual water from the solvent and the exchangeable carboxylic acid protons.

EXAMPLE 2

5-[4-[2-(N-Methyl-N-(2-pyridyl)amino)ethoxy] benzyl]thiazolidine-2,4-dione, maleic acid salt 5-[4-[2-(N-Methyl-N-(2-pyridyl)amino)ethoxy]benzyl] thiazolidine-2,4-dione, maleic acid salt (294.6 g, 0.825M) and maleic acid (95.8 g 0.825 m) were stirred in refluxing ethanol (2.71) until all the solid had dissolved. Decolourising charcoal was added and the hot solution filtered through celite, allowed to cool to room temperature with stirring. After cooling in a refrigerator at 0°–5° C. for several hours, the title compound was filtered, collected and dried at 50° C. under vacuum overnight to give 364.1 g (87%) of product, m.p. 119°–119.5° C.

The 1H NMR spectra was as for Example 1.

We claim:

1. A compound which is 5-[4-[2-(N-methyl-N-(2-pyridyl) amino)ethoxy]benzyl]thiazolidine-2,4-dione, maleic acid salt.

2. A pharmaceutical composition comprising a compound according to claim 1 and a pharmaceutically acceptable carrier.

3. A method for the treatment or prophylaxis of hyperglycemia which comprises administering the compound of claim 1.

4. A method for the treatment or prophylaxis of hyperlipidemia which comprises administering the compound of claim 1.

5. A process for preparing a compound according to claim 1, which comprises treating 5-[4-[2-(N-methyl-N-(2-pyridyl)amino)ethoxy]benzyl]thiazolidine-2,4-dione with maleic acid.

* * * * *

UNITED STATES PATENT AND TRADEMARK OFFICE
CERTIFICATE OF CORRECTION

PATENT NO. : 5,741,803
DATED : April 21, 1998
INVENTOR(S) : Colin Ripley Pool et al.

It is certified that error appears in the above-identified patent and that said Letters Patent is hereby corrected as shown below:

Title page,
Item [57], ABSTRACT,
Line 3, after "the" delete ",".
Line 5, delete "containin" and insert -- containing --.

Column 2,
Line 40, after "above" insert -- . --.

Signed and Sealed this

Fifteenth Day of July, 2003

JAMES E. ROGAN
*Director of the United States Patent and Trademark Office*